United States Patent [19]
Allington

[11] 3,989,948
[45] Nov. 2, 1976

[54] DUAL BEAM OPTICAL SYSTEM

[75] Inventor: Robert William Allington, Lincoln, Nebr.

[73] Assignee: Instrumentation Specialties Company, Lincoln, Nebr.

[22] Filed: June 9, 1975

[21] Appl. No.: 585,190

[52] U.S. Cl. .............................. 250/373; 250/575
[51] Int. Cl.² ...................... G01J 1/42; G01N 21/26
[58] Field of Search .......... 250/228, 578, 565, 575, 250/373; 356/204, 205, 206

[56] References Cited
UNITED STATES PATENTS

| | | | |
|---|---|---|---|
| 1,118,868 | 11/1914 | Kerschbaum | 250/504 |
| 2,411,672 | 11/1946 | van Den Akker | 250/204 X |
| 2,551,542 | 5/1951 | Marsh et al. | 250/365 |
| 3,463,927 | 8/1969 | Allington | 250/226 X |
| 3,490,875 | 1/1970 | Harmon et al. | 250/565 X |
| 3,552,863 | 1/1971 | Smith | 250/565 |
| 3,783,276 | 1/1974 | Allington | 250/578 X |

Primary Examiner—Alfred E. Smith
Assistant Examiner—T. N. Grigsby
Attorney, Agent, or Firm—Vincent L. Carney

[57] ABSTRACT

To compensate for variations in the intensity of light emitted from different locations within a lamp or in different directions from the lamp, a flat, thin, radiating member is positioned to receive intense light from the lamp and to radiate two divergent beams of light with proportional intensities in directions transverse to the member through collimating means oriented on the same light radiating spot. Light from the lamp, in one embodiment, is focused onto a spot on the side of the radiating member opposite the collimating means with an ellipsoidal reflector and, in another embodiment, the required intensity is obtained by positioning a lamp near the side of the radiating member opposite the collimating means.

46 Claims, 6 Drawing Figures

DUAL BEAM OPTICAL SYSTEM

This invention relates to optical systems and more particularly relates to light sources for generating and controlling beams of light for use in optical systems.

For some purposes, it is desirable to generate a plurality of beams of light of proportional intensities. One such purpose is to compare the light absorbing characteristics of two substances. For example, in liquid chromatography a comparison is made between a first beam of light transmitted through a solvent having solutes separated into zones and a second beam of light transmitted through pure solvent to locate solutes by the difference in light absorbing characteristics between the solutes and the pure solvent. The intensities of first and second beams of light are held as constant as possible with respect to one another except for changes caused by the solutes.

One class of light source suitable for these purposes includes a primary light source such as a mercury vapor lamp and an optical system for forming two beams of light from the primary light source. The intensity of the light supplied by the primary light source fluctuates in this class of light source and thereby causes some noise in the system.

The fluctuations in the intensity of light in this class of primary light source are of two general types, one type being a fluctuation in intensity in all directions such as when a point light source fluctuates and causes fluctuations in intensity from the point light source and the other type being fluctuations in the intensity in one direction with respect to the intensity transmitted in another direction at the same time. The second type of fluctuation occurs in mercury vapor ultraviolet lamps for two reasons, which are: (1) the light from one location within the lamp has, under some circumstances, an intensity that fluctuates with respect to the intensity of the light from another location within the lamp; and (2) mercury vapor moves by convection within the lamp and absorbs light being transmitted through it causing fluctuations in the absorption of light being transmitted in one direction with respect to absorption of the light being transmitted in another direction.

To reduce the noise caused by these reflections, one dual beam optical system disclosed in U.S. Pat. No. 3,783,276 includes: (1) an ellipsoidal reflector, having two sections separated along the major axis of the reflector, each with a different light-beam hole passing through it, which sections together form a prolate spheroid; (2) a primary source of light having its bright spot in one of the foci of the ellipsoidal reflector; and (3) a thin radiating member in the other foci of the ellipsoidal reflector, which radiating member transmits light through the two light-beam holes in the two sections of the ellipsoidal reflector.

The thin light-radiating member is translucent and has any one of three other arrangements to maintain the beams of light proportional, which are: (1) a light-diffusing surface; (2) a surface that flouresces; or (3) a surface that fluoresces and also diffuses light.

This dual beam optical system works quite well but has the disadvantage of being expensive. It is expensive because: (1) it requires two ellipsoidal reflectors positioned carefully with respect to the thin light-radiating member; (2) the flow cells through which the beams of light are sent in use of the optical system must be separated from each other and must be on opposite sides of the optical system, thus preventing use of economical dual flow cells; and (3) extra filters are necessary to remove certain unwanted frequencies of light.

Accordingly, it is an object of the invention to provide a novel optical system for controlling plural beams of light.

It is a further object of the invention to provide a novel apparatus for maintaining the intensities of a plurality of beams of light in a constant ratio to each other.

It is a still further object of the invention to provide a novel apparatus for radiating a plurality of beams of light having proportional light intensities from a radiating member, which apparatus is especially economical.

It is a still further object of the invention to provide a novel apparatus for compensating for spatial variations in the intensity of light from a light source, which does not require an expensive optical system.

In accordance with the above and further objects of the invention, an optical system includes: (1) a primary light source; (2) a translucent light-radiating member positioned to receive substantial light from the primary light source; and (3) an optical system arranged to form a plurality of beams of light from light radiated from the same spot on the light-radiating member.

The light-radiating member is thin and has any of three different types of surfaces to prevent fluctuations in light intensity, which are: (1) a light-diffusing surface; (2) a surface that fluoresces; or (3) a surface that fluoresces and also diffuses light. In one embodiment, the primary light source has its bright spot positioned in one focus of an ellipsoidal reflector and the light-radiating member is positioned in the other focus, the ellipsoidal reflector being one half of a prolate spheroid. In another embodiment, the radiating member is positioned adjacent to the primary light source, with no special optical system to focus light from the primary light source onto the light-radiating member.

In operation, high-intensity light from the light-radiating member passes through the light-radiating member and is: (1) diffused from its opposite surface; (2) emitted by fluorescense from the opposite surface; or (3) both diffused and emitted by fluorescense from the opposite surface. The light-radiating member may also include a material to filter certain frequencies of light from the primary light source as it is transmitted through the radiating member.

An optical system includes a plurality of lens or other geometrical collimating means which focus on the same spot on the light-radiating member to obtain a plurality of beams of light from that one spot. These beams of light are utilized in chromatography by passing them through flow cells or the like. Generally, since the beams of light are obtained from the same spot and the same spot radiates light with proportional intensities in different directions, there will be no fluctuations in the intensity of light transmitted in one direction with respect to the intensity of light transmitted in another direction. To obtain beams of light of substantially equal intensities directly from the light-radiating member, it is advantageous for the lens system to focus on the spot at directions forming equal angles with a normal since light emitted in any direction at the same angle to the light-radiating member is emitted with the same intensity.

As can be understood from the above summary, the optical system of this invention has the advantages of: (1) reducing directional fluctuations in the intensity of light applied to flow cells positioned on the same side of the light source; (2) being usable with dual flow cells; and (3) avoiding an unnecessarily complex focusing system for light from the primary light source and filtering systems for light from the radiating member.

The above noted and other features of the invention will be better understood from the following detailed description when considered with reference to the accompanying drawings in which.

GENERAL STRUCTURE AND OPERATION

Figure 1:
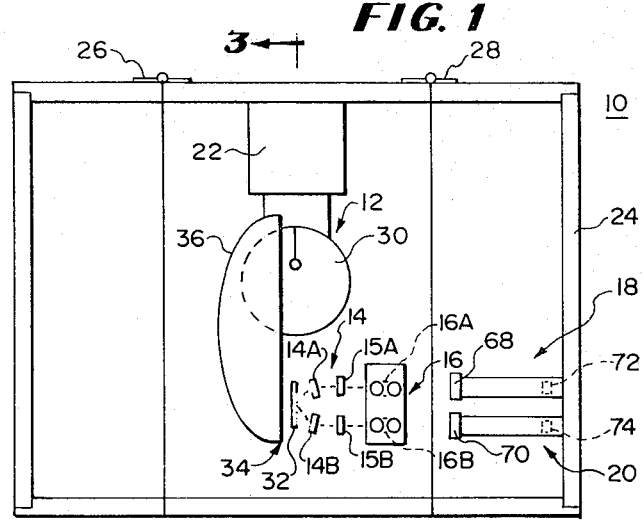
FIG. 1 is a plan view of an apparatus embodying the invention.

In FIG. 1, there is shown, in a plan view, a dual beam optical system 10 having as its principal parts a dual beam light source 12, a dual flow cell 16 having two light absorbance cells 16A and 16B, and first and second light measuring cells 18 and 20.

The dual beam light source 12 is mounted by a base 22 in a central location within a parallelepiped-shaped cabinet 24 and provides two beams of light to the dual flow cell 16, with the first light absorbance cell 16A being aligned with one beam from the light source 12 and the first light measuring cell 18 and with the second light absorbance cell 16B being aligned with another beam from the source 12 and the second light measuring cell 20. To provide access to the interior of the cabinet 24, its sides are hinged at 26 and 28, permitting it to be easily opened for assembly, repair and the replacement of parts when needed.

The dual beam optical system 10 is part of a photometric apparatus of the type requiring two matched beams of light. One such type of photometric apparatus, for example, locates organic solutes such as different proteins and amino acids and the like within a chromatographic column during fractionating of the column.

In this type of apparatus, the different organic solutes are located within the column by their different light absorbances, which are determined by transmitting a first beam of light from a dual beam source of light through the column containing the solute and a second beam of light from the dual beam light source through a sample of the solvent and comparing the intensities of the light in the two beams after they have been passed through the solute and pure solvent. However, it is understood that there are specific uses for the dual beam optical system 10 known to persons skilled in the art.

In the operation of the dual beam optical system 10, the first beam of light from the dual beam light source 12 impinges on the first light measuring cell 18 after passing through the first light absorbance cell 16A containing a solute to be located in a chromatographic column or to have its concentration determined and the second beam of light from the dual beam light source 12 impinges on the second optical measuring cell 20 after passing through the second light absorbance cell 16B containing only the solvent.

The first and second light measuring cells generate first and second electrical signals respectively in response to the light that impinges upon them and these signals are compared to provide a comparison between the light absorbance characteristics of the substances in the first and second light absorbance cells. This comparison is made by a circuit of the general type disclosed in U.S. Pat. No. 3,463,927 to Robert W. Allington for "Apparatus for Measuring Absorbance Differences."

DETAILED STRUCTURE

Figure 3:
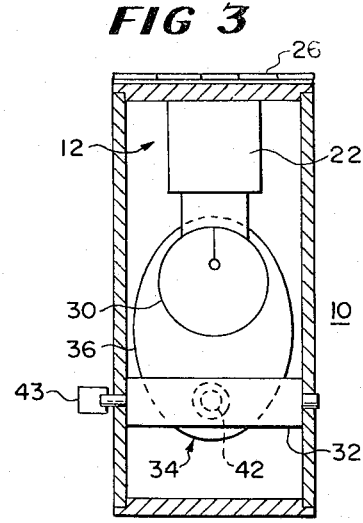
FIG. 3 is a side sectional view of the apparatus of FIG. 1 taken substantially along the line 3—3 in the direction of the arrows.
Figure 2:
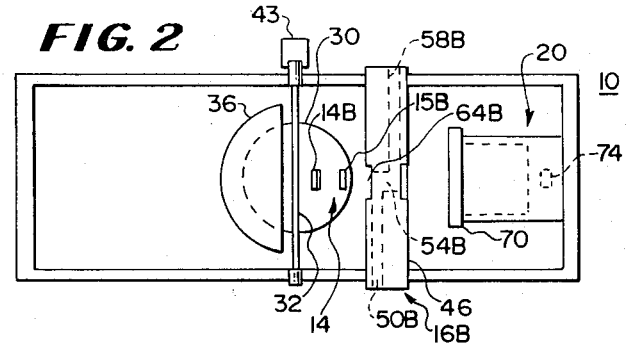
FIG. 2 is a front elevational view of the apparatus of FIG. 1.

The light source 12 includes a lamp 30, a light intensity balancer 32, a lens system 14 and, in the embodiments of FIGS. 1 through 3, an ellipsoidal reflector. The lens system 14 includes two lens 14A and 14B focused on the same light-radiating spot on the light intensity balancer 32 and two lens 15A and 15B which straighten the beams of light formed by corresponding lens 14A and 14B into parallel beams that are passed to the dual flow cell 16, where one beam of light passes through the light absorbance cell 16A and the other beam of light passes through the light absorbance cell 16B.

A less expensive dual beam optical system (not shown) does not include the lens 14A, 14B, 15A and 15B. In this system, the light paths through each half of the flow cell and each measuring cell are inclined with respect to each other and formed of straight lines which impinge upon the same spot on the light intensity balancer. In this embodiment, collimation is obtained by the aperture stop action of the light passage in each absorbance cell. As can be understood from a comparison of these embodiments, different light beam arrangements are possible to form any number of suitable beams, the important feature being the use of light from substantially the same area or spot on the radiating member for each beam.

To provide light for the first and second uniform beams of light, the lamp 30 is mounted to the base 22, which serves as a socket for electrical connection and is centrally located within the dual beam light source 12. The lamp 30 serves as a primary light source and may be any of several different types, the particular type generally being selected for its ability to provide light of the desired frequency.

In the preferred embodiment, the light 30 is a low-pressure mercury vapor lamp that emits ultraviolet light which is particularly useful in some photometric apparatuses such as those that measure or compare the optical density or light absorbance of certain solutions containing organic materials such as protein, amino acid or the like. However, other types of lamps may be used as a primary light source for other purposes. This invention has particular utility in photometric apparatuses in which the light emitted from some locations in the primary light source fluctuates in intensity with respect to light emitted from other locations or in which light emitted in some directions fluctuates in intensity with respect to light emitted in other directions.

To focus light of high intensity from the lamp 30 onto the light intensity balancer 32, the ellipsoidal reflector 36 has the general shape of half a prolate spheroid having its concave side facing the lamp 30, the light intensity balancer 32 and the dual flow cell 16. The bright spot of the lamp 30 is located in a first focus of the ellipsoidal reflector 36 to focus light on the second focus and the light intensity balancer 32 is located in the second focus to receive the light on a relatively-small light-radiating spot.

To cause the two divergent light beams emitted from the same light-radiating spot to have intensities that are in a constant ratio to each other even when the intensity of the light emitted by the lamp 30 varies over a period of time from location to location in the lamp or from direction to direction, the light intensity balancer 32 includes a transparent or translucent base with a flat light-radiating portion 42 (FIG. 3) mounted in the focus of the ellipsoidal reflector 36 and with both lens 14A, 14B focused on the same spot on the light-radiating portion 42 on the side of the light-radiating member opposite to that of the reflector 36 in such a manner that straight lines through the light-radiating spot and each lens 14A and 14B are transverse to the flat light-radiating portion and intersected at equal angles to the surface of the light-radiating member. The lens 15A and 15B are focused to receive light from corresponding ones of the lens 14A, 14B and are aligned with corresponding ones of the light-absorbance cells 16A, 16B.

To cause the intensities of the light in the light-radiating beams to be always in the same proportion, the light-radiating portion 42 of the light-intensity balancer 32 may include, in general, any surface or combination of surfaces that radiates light proportionally into a plurality of beams.

Because the light is directed from the light-radiating spot into two divergent directions, the light-radiating member should have its smallest dimension substantially parallel or at a very small angle to the light beams and this dimension should be sufficiently small to avoid any significant attenuation of the light passing through the light-radiating member by conversion to heat or losses in the collection of light for simple geometric reasons although there may be substantial light intensity drop because of diffuse radiation or fluorescent radiation in the direction away from the beams of light. Generally, it is less than one millimeter thick.

In one embodiment, the light-radiating portion 42 includes a translucent light-diffusing surface having a passive light-radiating means sufficiently thin to be translucent or having other light-scattering deformations. Herein, a passive light-radiating means does not emit light by the changes in the state of excitation of its atoms or molecules such as happens in incandescent or fluorescent radiators but only reradiates light. One type of passive light-radiating portion is a thin sheet of pure fused quartz with a sandblasted finish on both sides to provide a frosted ultraviolet transparent material. Another type of passive light-radiating portion is a strip of sintered Teflon (tetrafluoroethylene), still others are polycrystalline aluminum oxide or devitrified high silica glass.

The light-diffusing surface scatters light incident upon it in a random manner, causing the light to be radiated in accordance with Lambert's cosine law, with the intensity being proportional to the cosine of the angle the light makes with a normal to the light-diffusing surface regardless of its location of origin in the lamp 30. Accordingly, the ratio of the intensities of the light in all beams is constant because the beams are all at constant angles to the emitting surface and beams formed of light radiated at the same angle have equal intensities.

In another embodiment, the light equalizing portion 42 includes for this purpose fluorescent particles in a layer sufficiently thin to be translucent or a transparent sheet of fluorescent material mounted to the transparent or translucent base plate of the light intensity balancer 32. The fluorescent particles or sheet emit light in all directions so that each point contributes proportionately to the first and second beams of light. The fluorescent particles also create a diffusing surface, causing diffused light of the frequency emitted by the lamp 30 as well as light emitted by fluorescense of the particles to be directed into the first and second beams of light.

The frequencies to be passed through the light-absorbance cells 16A and 16B and to the photocells within the light-measuring cells 18 and 20 are selected by including filters in the path of the beam of light to selectively absorb those frequencies of light that are not to be passed to the photocells. Since the filters are easily changed, the presence of two different ranges of frequencies of light, one from fluorescense of the particles and the other from diffusion of light, each of which is useful in a different application of the dual beam optical system, enables the dual beam optical system to be easily adapted to different applications.

To provide for convenient selection of different frequencies for the light beams for different applications in the preferred embodiment the light-intensity balancers are readily replaceable so that any of several light-intensity balancers, each having different fluorescent materials that emit light at different frequencies, may be selected for use in the dual beam optical system. In another embodiment (not shown) the light-intensity balancers are readily adjustable in position within the ellipsoidal reflector and include a plurality of different fluorescent materials at different locations that emit light at different frequencies. The light-intensity balancers are adjusted to position a selected one of the different fluorescent materials into the focus of the ellipsoidal reflector to select the frequency of light to emit into the beams.

In the preferred embodiment, the light-intensity balancer 32 is formed as a replaceable, removable strip having an enlarged gripping portion 43 on one end and the walls of the cabinet 24 include aligned slots large enough to receive all but the handle 43 so that the light-intensity balancer 32 may be inserted through the slots which hold it in position. When it is in position, the light-radiating portion 42 is in a focus of the reflector 36 and the handle 43 is outside the cabinet 24 so that the light-intensity balance 32 can be easily removed.

Some light-intensity balancers have a passive diffusing light-radiating portion 42 and others a fluorescent light-radiating portion, with the light-intensity balancers having the fluorescent light-radiating portion being sufficiently thick to block all 254 nanometer light and the filters 68 and 70 being permanent and passing a band of light between approximately 250 nanometers and 290 nanometers so that the dual beam optical system can provide either 254 nanometer beams of light or 280 nanometer beams of light by using, for the 254 nanometer light, a light-intensity balancer having a diffusing portion 42 and, for the 280 nanometer light, a fluorescent portion 42. This embodiment is economical and can be easily adjusted for either 254 or 280 nanometer light by changing strips 32. Of course, in both of these embodiments, different light filters may be selected in accordance with the frequencies that are to be used to provide better removal of noise if desired although this is not required.

In the preferred embodiment, the substrate of the light-intensity balancer 32 is Teflon (PTFE). In another embodiment, it is quartz because quartz is transparent to ultraviolet light which light is especially useful in the preferred embodiment. However, other materials can obviously be used as the substrate.

There are many known methods for fastening particles to the surface of a substrate or for deforming a substrate to cause it to diffuse light. For example, Teflon particles may be fused together to form a Teflon member which is translucent but includes different density areas and deformations that diffuse light or particles may be fused within the Teflon strip. Moreover, particles may be mounted by precipitation of an adhesive binder or held between two sections of a quartz substrate. The substrate may also be deformed by scratching or roughing its surfaces to cause it to diffuse light when particles are not fastened to it.

Particularly useful fluorescent materials for the light-intensity balancer 32 are microcrystalline lanthanum fluoride with cerium activation as described in U.S. Pat. No. 2,450,548 to Gishoff or calcium lithium silicate, lead activated phosphor.

As best shown in FIG. 2, the light-absorbance cells 16A and 16B are each enclosed in a rectangular housing 46 and include respective ones of two, transparent, tubular, generally Z-shaped passageways, each passageway being identical, one of the passageways 50B, 54B, 58B being shown in FIG. 2, with each passageway including: (1) a respective one of the vertical entrance channels 50A and 50B extending from a point below the dual beam light source 12 in a direction substantially parallel to the light-intensity balancer 32 to a point opposite to a respective one of the lens 15A or 15B; (2) a respective one of two light-absorbing channels 54A or 54B extending in a direction aligned with one of the lens 15A or 15B; and (3) a respective one of the two outlet channels 58A or 58B extending vertically from points opposite to the lens 15 and parallel to the light-intensity balancer 32 to points above the dual beam light source.

To permit the first and second beams of light from the dual beam light source to pass from the lens through the light-absorbing channels 54, the light-absorbing channels 54 have transparent windows 64 on one side and transparent windows 66 on the other side aligned with the lens 15 to permit light to pass through the housing 46.

To measure the light absorbance or transmittance of the fluid in the light-absorbance channels 58, the first and second light measuring cells 18 and 20 receive the first and second beams of light respectively after they have passed through the light-absorbance channels 58A and 58B respectively of the first and second light-absorbance cells 16A and 16B. Each of the first and second light-measuring cells 18 and 20 includes a different one of the filters 68 and 70 and a different one of the two photocells 72 and 74, mounted in positions aligned with the first and second beams of light so that the first and second beams of light each pass through one of the filters 68 and 70 before exciting a respective one of the two photocells 72 and 74.

The photocells 72 and 74 are part of a circuit for comparing the light impinging upon them and providing an indication of the relative optical density of the fluid in the light-absorbance cells 16A and 16B for the purpose of locating or identifying a solute in the fluid flowing through one of the light-absorbance cells as described in greater detail in the aforementioned U.S. Pat. No. 3,463,927. The filters are similar in some respects to those described in U.S. Reissue Pat. No. 26,638.

Figure 4:
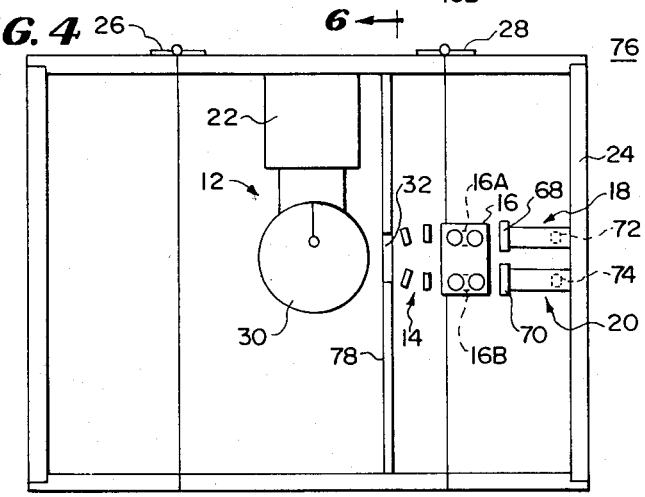
FIG. 4 is a plan view of another embodiment of apparatus in accordance with the invention.
Figure 6:
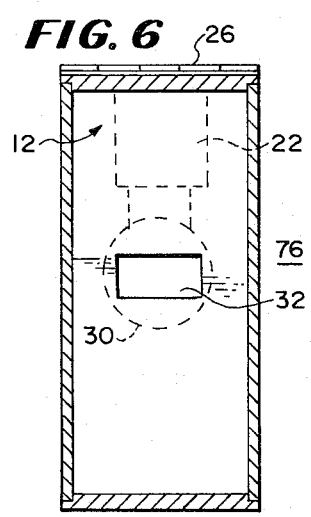
FIG. 6 is a sectional view of the apparatus of FIG. 4 taken substantially along the line 6—6 in the direction of the arrows.
Figure 5:
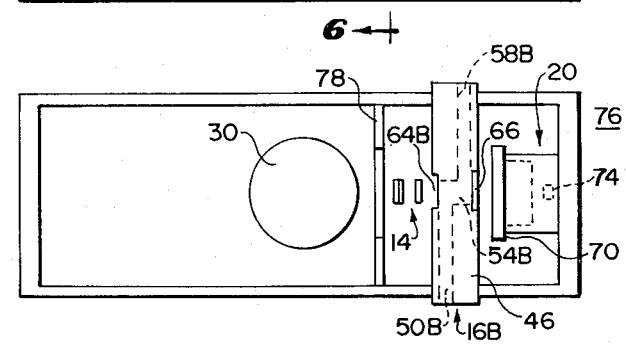
FIG. 5 is a front elevational view of the apparatus of FIG. 4.

In FIGS. 4 through 6, there is shown another embodiment of dual beam optical system which is a variation of the embodiment 10 using a substitute for the reflector 36. The parts of this embodiment which are identical to the embodiment of FIG. 10 have the same reference numbers and new parts have different reference numbers.

In the embodiment of FIGS. 4 through 6, the ellipsoidal reflector 36 is omitted and to provide sufficient light intensity to the light-intensity balancer 32, the light-intensity balancer is positioned immediately adjacent the lamp 30 and held within the light shield 78 which blocks all light except that emitted directly by the lamp 30 against the light-intensity balancer 32. This arrangement operates similarly to the embodiment of FIGS. 1-3 but is less expensive because the reflector need not be included and there is less difficulty in positioning the lamp and light-intensity balancer 32 since it is not necessary to position them in the foci of an ellipsoidal reflector.

DETAILED OPERATION

Before operating the dual beam optical systems 10 and 76, the filters 68 and 70 are selected and inserted into the first and second light-measuring cells 18 and 20 (FIGS. 1 and 4). Generally, the filters are selected for use in accordance with the type or types of organic solutes that are to be located in fluid that is flowing from a chromatographic column through the first light-absorbance cell 16A, but of course, the filters are chosen according to other criteria for other applications of the dual beam optical system. In the preferred embodiment, the filters pass a band substantially between 250 and 290 nanometers and are usable to provide either 254 or 280 nanometer beams of light.

In the operation of the dual beam optical systems 10 and 76, a solvent containing a solute is pumped through the light-absorbance cell 16A and pure solvent is pumped through the second light-absorbance cell 16B. While the solute is flowing through the light-absorbance channel 58A of the first light-absorbance cell 16A and the pure solvent is flowing through the light-absorbance channel 58B of the second light-absorbance cell 16B, the first beam of light is transmitted through the light-absorbance channel 58A to the first light-measuring cell 18 and the second beam of light is transmitted through the light-absorbance channel 58B to the second light-measuring cell 20, with the first and second beams of light having proportional light intensities. The first light-measuring cell 18 and the second light-measuring cell 20 compare the intensity of the light in the first and second beams of light to obtain information about the solute flowing the first light-absorbance channel 58A.

To generate the first and second beams of light, the lamp 30 radiates light, which in the preferred embodiment is ultraviolet light, onto the light-intensity balancer 32. Since the bright spot of the lamp 30 is in one focus and the light-radiating portion 42 of the light-intensity balancer is in the other focus of the ellipsoidal reflector 36 in the embodiment of FIGS. 1 through 3 and since the lamp is positioned adjacent to the light-intensity balancer 32 in the embodiment of FIGS. 4 through 6, light of high intensity is radiated from the lamp 30 to the light-radiating portion 42 of the light-intensity balancer 32.

In an embodiment in which the light-intensity balancer 32 is a translucent diffusing surface that diffuses the light radiated to it and reradiates it, light is radiated from the light-radiating spot on the light-radiating portion 42 in accordance with Lambert's cosine law and is proportional in intensity in every direction from the same spot. Similarly, in an embodiment in which the light-balancing member 32 includes a thin transparent or translucent layer of fluorescent particles, which diffuse light and fluoresce, the diffused light contributes proportionally to light emitted in all directions from the opposite side of the light-balancing member 32 and the phosphor emits light independently of the direction of the light and in an embodiment in which the light-balancing member is a sheet of clear phosphor material light is also emitted proportionally in all directions from the same spot by the phosphor.

Light which passes through or is emitted from the light-balancing member 32, is received through the lens system 14, with the lens 14A and 14B focusing on the same spot to provide light to the lens 15A and 15B respectively in two beams. These two beams are transmitted through the flow cells 16A and 16B and into the light-measuring cells 18 and 20 where they pass through the filters 68 and 70 respectively. The filters 68 and 70 select a single spectral line to transmit to the photocells 72 and 74 in accordance with the particular application of the dual beam optical system, and the photocells generate electrical signals related to the amount of light absorbed in the flow cells for comparison.

From the above description it can be understood that the dual beam optical system of this invention has several advantages, such as the advantage of being economical to construct and providing low-noise-level level beams of light even though the primary light source emits light that fluctuates in intensity in each direction and in different directions with respect to each other.

It is economical for several reasons, such as: (1) in one embodiment, it only requires one half of an ellipsodial reflector thus reducing the cost of an ellipsoidal reflector and the cost of positioning the radiating member and light source within the foci of the ellipsoidal reflector; (2) in another embodiment, it does not require a reflector and the alignment cost is still lower; (3) some filtering takes place within the light-radiating member, especially with a fluorescent member which absorbs the existing radiation, since light must pass through it before being focused into beams thus reducing the cost of filters; and (3) dual flow cells may be used rather than separate flow cells.

Although a specific embodiment of the invention has been described with some particularity many modifications and variations in the embodiment are possible in the light of the above teachings. It is therefore to be understood that within the scope of the appended claims, the invention may be practiced otherwise than as specifically described without departing from the invention.

What is claimed is:

1. Apparatus for directing light from a light source into a plurality of paths, comprising:

a light member having first and second surfaces;

said light-radiating member being positioned to receive light from said light source with substantial light intensity on at least a first spot on said first surface of said light-radiating member;

said light-radiating member being capable of passing light from said first spot on said first surface to a second spot on said second surface, whereby a substantial amount of light is radiated from said second spot by said light-radiating member;

said light-radiating member including light-radiating means for radiating light along at least a first and a second of said paths from said second spot in response to said light from said light source with a substantially constant ratio of the intensity of the light in said first path to the intensity of the light in said second path, which ratio is substantially independent of fluctuations in the light of said light source;

light-beam-forming means for transmitting light from the second spot on said light-radiating member into said plurality of paths;

said light-beam-forming means being on the opposite side of said light-radiating member from said first spot.

2. Apparatus according to claim 1 in which said light-radiating member is a frosted ultraviolet transparent material.

3. Apparatus according to claim 1 in which said light-radiating member is devitrified high silica glass.

4. Apparatus according to claim 1 in which said light-radiating member is polycrystalline aluminum oxide.

5. Apparatus according to claim 1 further including at least first and second photocells, said first photocell being positioned in one of said plurality of paths and said second photocell being positioned in another of said plurality of paths.

6. Apparatus according to claim 1 in which:

said light source includes focusing means for focusing light from said light source onto a spot on said light-radiating member, whereby a substantial amount of light is radiated by said light-radiating member;

said focusing means including an ellipsoidal reflector having first and second foci;

said light-radiating member being located in said first focus of said ellipsoidal reflector; and said light source including means for emitting light from said second focus of said ellipsoidal reflector.

7. Apparatus according to claim 6 in which:

said light-radiating member is a passive light-radiating means;

said passive light-radiating means includes means for substantially diffusing light.

8. Apparatus according to claim 6 in which:

said light-radiating member is a fluorescent means for emitting light at a first frequency when impinged upon by light having a second frequency; and said light source includes means for emitting light of said second frequency.

9. Apparatus according to claim 1 in which:

said light-radiating member is a passive light-radiating means; and said passive light-radiating means includes means for substantially diffusing light.

10. Apparatus according to claim 9 further including at least first and second photocells, said first photocell being positioned in one of said plurality of paths and said second photocell being positioned in another of said plurality of paths.

11. Apparatus according to claim 9 in which said apparatus further includes means for removably mounting said light-radiating member.

12. Apparatus according to claim 9 in which said light-beam-forming means includes light-collimating means for collimating light from the same spot on said light-radiating member into said plurality of paths.

13. Apparatus according to claim 12 in which said light collimating means includes:
light detecting means for providing an electrical signal in response to light from said light-radiating member; and
flow-cell means having internal walls forming a flow path for fluids:
said light detecting means and flow-cell means including aperture stops forming straight-line light paths from said one spot through said flow-cell means and into said light detecting means.

14. Apparatus according to claim 1 in which said light-radiating member is a thin tetrafluoroethylene member having light-diffusing properties.

15. Apparatus according to claim 14 in which said tetrafluoroethylene member includes selective light-absorbing material, whereby said member filters light from said light source.

16. Apparatus according to claim 14 in which said tetrafluoroethylene member is formed of fused tetrafluoroethylene particles.

17. Apparatus according to claim 14 in which said light source includes:
focusing means for focusing light onto a spot on said light-radiating member, whereby a substantial amount of light is radiated by said light-radiating member;
said focusing means including an ellipsoidal reflector having first and second foci;
said light-radiating member being located in said first focus of said ellipsoidal reflector; and
said light source including means for emitting light from said second focus of said ellipsoidal reflector.

18. Apparatus according to claim 1 in which said light-beam-forming means includes light-collimating means for collimating light from the same spot on said light-radiating member into said plurality of paths.

19. Apparatus according to claim 18 in which said light-radiating member is a thin tetrafluoroethylene member having light-diffusing properties.

20. Apparatus according to claim 18 in which said light-radiating member is a frosted ultraviolet transparent material.

21. Apparatus according to claim 18 in which said light-radiating member is devitrified high silica glass.

22. Apparatus according to claim 18 in which said light-radiating member is polycrystalline aluminum oxide.

23. Apparatus according to claim 18 in which said light source includes:
focusing means for focusing light from said light source onto a spot on said light-radiating member, whereby a substantial amount of light is radiated by said light-radiating member;
said focusing means including an ellipsoidal reflector having first and second foci;
said light-radiating member being located in said first focus of said ellipsoidal reflector; and
said light source including means for emitting light from said second focus of said ellipsoidal reflector.

24. Apparatus according to claim 18 in which said light collimating means includes:
light detecting means for providing an electrical signal in response to light from said light-radiating member; and
flow-cell means having internal walls forming a flow path for fluids;
said light detecting means and flow-cell means including aperture stops forming straight-line light paths from said one spot through said flow-cell means and into said light detecting means.

25. Apparatus according to claim 24 in which said light source includes:
focusing means for focusing light from said light source onto a spot on said light-radiating member, whereby a substantial amount of light is radiated by said light-radiating member;
said focusing means including an ellipsoidal reflector having first and second foci;
said light-radiating member being located in said first focus of said ellipsoidal reflector; and
said light source including means for emitting light from said second focus of said ellipsoidal reflector.

26. Apparatus according to claim 24 in which:
said plurality of light-radiating members include at least first and second interchangeable light-radiating members;
said first light-radiating member being a passive light-radiating means for substantially diffusing light from the light source and said second light-radiating member being a fluorescent means for emitting light at a first frequency when impinged upon by light having a second frequency, said light source including means for emitting light of said second frequency.

27. Apparatus according to claim 1 in which:
said light-radiating member is a fluorescent means for emitting light at a first frequency when impinged upon by light having a second frequency; and
said light source includes means for emitting light of said second frequency.

28. Apparatus according to claim 27 further including at least first and second photocells, said first photocell being positioned in one of said plurality of paths and said second photocell being positioned in another of said plurality of paths.

29. Apparatus according to claim 27 in which said apparatus further includes means for removably mounting said light-radiating member.

30. Apparatus according to claim 27 in which:
said plurality of light-radiating members include at least first and second interchangeable light-radiating members;
said first light-radiating member being a passive light-radiating means for substantially diffusing light from the light source and said second light-radiating member being a fluorescent means for emitting light at a first frequency when impinged upon by light having a second frequency, said light source including means for emitting light of said second frequency.

31. Apparatus according to claim 27 in which said light-radiating member includes means for blocking light having a wavelength substantially of 254 nanometers.

32. Apparatus according to claim 31 further including:
a plurality of photocells;
said photocells being sensitive to a predetermined frequency;
different ones of said photocells being mounted in line with different ones of said filters and said paths; and
said filters including means for providing light of said predetermined frequency to said photocells in response to light substantially in the wavelength range of 250 to 290 nanometers.

33. Apparatus according to claim 27 in which said light-beam-forming means includes light-collimating means for collimating light from the same spot on said light-radiating member into said plurality of paths.

34. Apparatus according to claim 33 in which said light collimating means includes:
light detecting means for providing an electrical signal in response to light from said light-radiating member; and
flow-cell means having internal walls forming a flow path for fluids;
said light detecting means and flow-cell means including aperture stops forming straight-line paths from said one spot through said flow-cell means and into said light detecting means.

35. Apparatus according to claim 27 in which said light-radiating member includes means for substantially diffusing light.

36. Apparatus according to claim 35 in which said means for substantially diffusing light comprises a plurality of particles.

37. Apparatus according to claim 36 in which:
said plurality of particles comprise fluorescent means for emitting light at a first frequency when impinged upon by light having a second frequency;
said light source including means for emitting light of said second frequency, whereby diffused light of said second frequency and fluorescent light of said first frequency are directed along said plurality of paths.

38. Apparatus according to claim 37 further including:
a plurality of interchangeable filter mounting means;
each of said interchangeable filter mounting means being mounted in a different one of said plurality of paths; and
said filter mounting means being adapted to receive filters blocking a selected one of said first and second frequencies of light.

39. Apparatus according to claim 38 in which said fluorescent means comprises means for emitting light having a wavelength substantially in the range of 270 to 290 nanometers, and said light source is an ultraviolet lamp.

40. Apparatus according to claim 1 in which said apparatus further includes means for removably mounting said light-radiating member.

41. Apparatus according to claim 40 in which said mounting means includes means for selectively mounting any one of a plurality of different light-radiating members.

42. Apparatus according to claim 41 in which:
said plurality of light-radiating members include at least first and second interchangeable light-radiating members;
said first light-radiating member being a passive light-radiating means for substantially diffusing light from the light source and said second light-radiating member being a fluorescent means for emitting light at a first frequency when impinged upon by light having a second frequency, said light source including means for emitting light of said second frequency.

43. Apparatus according to claim 42 further including light filter means for passing light having wavelength over the range of 250 through 285 nanometers.

44. Apparatus according to claim 42 in which said fluorescent means absorbs 254 nanometers light.

45. Apparatus according to claim 44 in which said fluorescent means emits light substantially within 270 to 290 nanometers.

46. Apparatus according to claim 45 in which said light filters are not interchangeable.

* * * * *

UNITED STATES PATENT AND TRADEMARK OFFICE
CERTIFICATE OF CORRECTION

PATENT NO. : 3,989,948
DATED : November 2, 1976
INVENTOR(S) : Robert William Allington It is certified that error appears in the above-identified patent and that said Letters Patent are hereby corrected as shown below:

Column 1, line 59, change "flouresces" to "fluoresces".

Column 6, line 3, change "light equalizing portion" to "light-radiating portion".

Column 6, line 53, change "balance" to "balancer".

Column 9, line 44, omit the word "level" at the beginning of the line.

Column 9, line 49 and 50, change the word "ellipsodial" to "ellipsoidal".

Column 10, line 4, change "light member" to "light-radiating member".

Column 10, line 25, after the semicolon, add the word "and".

Column 10, line 56, after the semicolon, add the word "and".

Column 11, line 12, after the word "forming", omit the hyphen.

Column 11, line 19, after the semicolon, omit the word "and".

Column 11, line 21, after the semicolon, add the word "and".

Column 12, line 11, after the semicolon, omit the word "and".

UNITED STATES PATENT AND TRADEMARK OFFICE
CERTIFICATE OF CORRECTION

PATENT NO. : 3,989,948

DATED : November 2, 1976

INVENTOR(S) : Robert William Allington

It is certified that error appears in the above-identified patent and that said Letters Patent are hereby corrected as shown below:

Column 12, line 13, after the semicolon, add the word "and".

Column 13, line 30, change "straight-line paths" to "straight-line light paths".

Column 13, line 42, after the semicolon, add the word "and".

Column 14, line 27, after the semicolon, add the word "and".

Signed and Sealed this

Twenty-fifth Day of December 1979

[SEAL]

Attest:

Attesting Officer

SIDNEY A. DIAMOND

Commissioner of Patents and Trademarks